United States Patent [19]

Torii et al.

[11] 4,238,615
[45] Dec. 9, 1980

[54] CYCLOPENTANONE INTERMEDIATES 2-(BENZOTHIAZOLYL-2)

[75] Inventors: Sigeru Torii; Hideo Tanaka; Toshihiro Kudai, all of Okayama, Japan

[73] Assignee: Otsuka Kagaku Yakuhin Kabushiki Kaisha, Osaka, Japan

[21] Appl. No.: 884,222

[22] Filed: Mar. 7, 1978

[51] Int. Cl.³ .................................... C07D 277/64
[52] U.S. Cl. .................................. 548/170; 252/522 R; 546/122; 568/379
[58] Field of Search ........................ 260/306; 548/170

[56] References Cited

U.S. PATENT DOCUMENTS 2,211,623  8/1940  Lichty ............................ 260/306

OTHER PUBLICATIONS

Rozhkova C. A. 85 1976 Abst. 1876222 and Index page. Abrt. of Matev. Vses, Sov. Def. Des. s-hh.Kult. 1st 1972 (Pub. 1974) pp. 137–143.
Joulain Parfums, Cosmetiques, Aromes, 12 Nov./Dec. 1976 pp. 53–63.
Sakai "Org. Syn. Chem." (Yuki Gosei Kagaku) vol. 29, No. 3, pp. 205–226 (1971) (Japanese).
Buchi et al., J. Org. Chem. 36 (14) pp. 2021–2023, 1971.
Stork et al., "J. A. C. S." 97 (11) pp. 3258–3260, 1975.

*Primary Examiner*—Donald G. Daus
*Assistant Examiner*—D. B. Springer
*Attorney, Agent, or Firm*—Armstrong, Nikaido, Marmelstein & Kubovcik

[57] ABSTRACT

2-Substituted-cyclopentanone derivatives represented by the formula

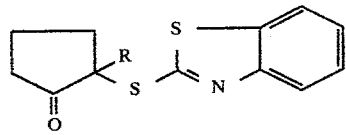

are prepared by subjecting a 2-benzothiazolylsulfenamide derivative represented by the formula

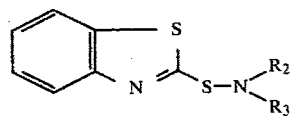

and cyclopentanone to condensation reaction, or by reacting the resulting condensation product with a hydrocarbon halide represented by the formula
$R_1X$.

4 Claims, No Drawings

CYCLOPENTANONE INTERMEDIATES 2-(BENZOTHIAZOLYL-2)

This invention relates to novel 2-substituted-cyclopentanone derivatives and to processes for preparing the same.

The derivatives of this invention are novel compounds which have not been disclosed in literature and which are represented by the formula

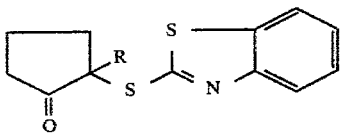

wherein R is hydrogen or $R_1$, the group $R_1$ being alkyl having from 1 to 6 carbon atoms, alkenyl having from 2 to 6 carbon atoms or alkynyl having from 2 to 6 carbon atoms. The compounds are very useful as intermediates for producing methyl jasmonate, cis-jasmone, etc. which are well known as main fragrant components of jasmine oil derived from plants as a high-quality perfume.

The compounds of this invention are prepared by various processes. Preferably, for example, the compound represented by the formula (I) wherein R is hydrogen (hereinafter referred to as "Compound (I-a)") is prepared by subjecting a 2-benzothiazolylsulfenamide derivative represented by the formula

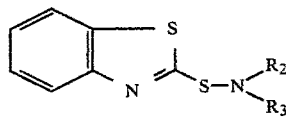

wherein $R_2$ and $R_3$ are each hydrogen, alkyl having from 1 to 4 carbon atoms, cyclohexyl or phenyl except when $R_2$ and $R_3$ are both hydrogen; when one of $R_2$ and $R_3$ is cyclohexyl or phenyl, the other is hydrogen; and $R_2$ and $R_3$, when taken together, may form a tetramethylene group, pentamethylene group or —CH$_2$CH$_2$OCH$_2$CH$_2$—group; and cyclopentanone to condensation reaction. The compounds represented by the formula (I) wherein R is $R_1$ (hereinafter referred to as "Compounds (I-b)") are prepared by reacting Compound (I-a) with a hydrocarbon halide represented by the formula $R_1X$ (III)

wherein $R_1$ is as defined above, and X is halogen.

Specific examples of 2-benzothiazolylsulfenamide derivatives of the formula (II), which are known compounds useful as starting materials in the present invention, are N-ethyl-2-benzothiazolylsulfenamide, N-propyl-2-benzothiazolylsufenamide, N,N-dimethyl-2-benzothiazolylsulfenamide, N,N-diethyl-2-benzothiazolylsulfenamide, N-n-butyl-2-benzothiazolylsulfenamide, N-sec.-butyl-2-benzothiazolylsulfenamide, N-tert.-butyl-2-benzothiazolylsulfenamide, N-phenyl-2-benzothiazolylsulfenamide, N-cyclohexyl-2-benzothiazolylsulfenamide, N-tetramethylene-2-benzothiazolylsulfenamide, N-pentamethylene-2-benzothiazolylsulfenamide, N-oxydiethylene-2-benzothiazolylsulfenamide, etc.

The other starting material used in this invention, namely cyclopentanone, is a known compound which can be easily prepared by heating readily available adipic acid with barium hydroxide.

The ratio of cyclopentanone to the compound of the formula (II) is not particularly limited but is widely variable. Usually one to 10 moles, preferably about 1.1 to about 2 moles, of the former is used per mole of the latter. The condensation reaction is conducted preferably in an organic solvent. Examples of useful organic solvents are hydrocarbon halides such as methylene chloride, chloroform and dichloroethane; aromatic hydrocarbons such as benzene, toluene and xylene; aliphatic cyclic ethers such as tetrahydrofuran and dioxane; etc. The reaction, which will proceed in the absence of a catalyst, can be accelerated by the use of an acid catalyst. Examples of useful acid catalysts are formic acid, acetic acid, p-toluenesulfonic acid and like organic acid, among which formic acid and acetic acid are preferable to use. The acid catalyst is used usually in an amount of about 1% by weight based of cyclopentanone. The reaction is carried out at room temperature or with heating, usually at 20° to 150° C., preferably at 50° to 110° C., for 1 to 20 hours, although the reaction time is dependent on the reaction conditions. In this way, Compound (I-a), namely 2-(benzothiazolyl-2-mercapto)cyclopentanone, is prepared according to this invention. The compound obtained is purified by usual methods including extraction and filtration.

Useful hydrocarbon halides of the formula (III) for the preparation of Compounds (I-b) are a wide variety of those heretofore known, such as methyl bromide, ethyl bromide, propyl bromide, 2-propenyl bromide, 2-propynyl bromide, pentyl bromide, cis-pentenyl bromide, 2-pentynyl bromide and hexyl bromide. Also useful are the chlorides and iodides corresponding to these bromides.

The ratio of Compound (I-a) to the compound of the formula (III) is not particularly limited; the latter can be used in a large excess relative to the former. It is advantageous, however, to use usually one to 2 moles, preferably one to 1.3 moles, of the latter per mole of the former. Preferably the reaction is conducted in an organic solvent. Examples of useful organic solvents are aliphatic ketones such as acetone, methyl ethyl ketone and methyl isobutyl ketone; alcohols such as methanol and ethanol; aromatic hydrocarbons such as benzene, toluene and xylene; aliphatic cyclic ethers such as tetrahydrofuran and dioxane; aliphatic hydrocarbon halides such as dichloroethane and trichlene; etc. These solvents are usable in admixture. The reaction, when conducted in the presence of a basic catalyst, can be completed within a shortened period of time. Although a metal hydride, metal amide or the like is usable as such a basic catalyst, it is preferable to use sodium carbonate or potassium carbonate which is available easily and inexpensively. Usually one to 10 moles, desirably 1.5 to 4 moles of the basic catalyst is used per mole of Compound (I-a). When the halogen of the compound of the formula (III) used is chlorine or bromine, the desired compound can be obtained in increased yields by conducting the reaction also in the presence of 0.1 to 1.0 mole of an iodide, such as sodium iodide, potassium iodide or lithium iodide, per mole of Compound (III), in addition to the basic catalyst mentioned. The reaction between Compound (I-a) and the compound (III), which can be carried out at widely varying temperatures, is preferably conducted approximately at the boiling point of the solvent used. The reaction time is usually 6 to 24 hours. It is desirable to continuously heat the reaction system until the completion of the reaction is confirmable by thin-layer chromatography. In this way, Compounds (I-b) are prepared according to the present invention. The compounds obtained are purified by conventional methods including extraction and filtration. Typical of Compounds (I-b) are 2-methyl-2-(benzothiazolyl-2-mercapto)cyclopentanone, 2-ethyl-2-(benzothiazolyl-2-mercapto)cyclopentanone, 2-propyl-2-(benzothiazolyl-2-mercapto)cyclopentanone, 2-butyl-2-(benzothiazolyl-2-mercapto)cyclopentanone, 2-pentyl-2-(benzothiazolyl-2-mercapto)cyclopentanone, 2-hexyl-2-(benzothiazolyl-2-mercapto)cyclopentanone, 2-allyl-2-(benzothiazolyl-2-mercapto)cyclopentanone, 2-(cis-2-pentenyl)-2-(benzothiazolyl-2-mercapto)cyclopentanone, 2-propargyl-2-(benzothiazolyl-2-mercapto)cyclopentanone, 2-(2-pentynyl)-2-(benzothiazolyl-2-mercapto)cyclopentanone, etc.

When heated, Compound (I-b) can be readily converted to a compound represented by the formula

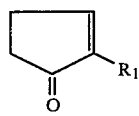 (IV)

wherein $R_1$ as defined above. This reaction may be conducted without using any solvent or in an organic solvent. Examples of useful solvents are dioxane and like aliphatic cyclic ethers, toluene, xylene and like aromatic hydrocarbons, dimethylformamide, dimethyl sulfoxide, etc. The reaction can be accelerated when conducted in the presence of an acid catalyst. Examples of useful acid catalysts are organic sulfonic acids such as benzenesulfonic acid and p-toluenesulfonic acid; mineral acids such as sulfuric acid, hydrochloric acid and phosphoric acid; strongly acidic ion exchange resins, etc. Generally 0.1 to 10% by weight, preferably 0.5 to 5% by weight, of the acid catalyst is used based on Compound (I-b). The reaction is conducted usually at a temperature of 50° to 150° C., preferably 100° to 130° C., generally for one to 2 hours. The compounds of the formula (IV) are very useful as intermediates for the preparation of methyl jasmonate, cis-jasmone, etc. which are well known as main fragrant components of jasmine oil derived from plants as a high-quality perfume. As compared with the known process, the process described above has the advantages of: (1) giving the desired compound in two to three times the conventional yield with higher purity, (2) involving a reduced number of steps which can be practiced with greater ease, and (3) using a material which is easily available.

This invention will be described below in greater detail with reference to examples and reference examples.

EXAMPLE 1

A 20 g quantity of N-cyclohexyl-2-benzothiazolylsulfenamide is dissolved in 50 ml of methylene chloride, and the solution is heated to about 50° C. Subsequently 1 g of acetic acid is added to the solution, and 13.5 g of cyclopentanone is further added thereto at a time. The mixture is allowed to react at the same temperature for 2 hours with stirring. The reaction mixture is cooled to room temperature, placed into a separating funnel, washed with water and thereafter extracted with 5% aqueous solution of hydrochloric acid three times. The condensation product dissolved in the aqueous solution of hydrochloric acid is neutralized with sodium bicarbonate and then reextracted with ethyl acetate. The extract is dried over magnesium sulfate and filtered. Concentration of the filtrate in vacuo gives 14.6 g of 2-(benzothiazolyl-2-mercapto)cyclopentanone in the form of white crystals, yield 80%.

Melting point: 115°–116° C.

IR (Nujol): 3040, 2660, 1745, 1430, 1403, 1380, 1315, 1275, 1243, 1165, 1150, 1125, 1080, 1025, 1000, 938, 820, 750, 725 cm.$^{-1}$ NMR (CDCl$_3$): $\delta$1.6–3.0 (broad m, 6H, —CH$_2$—), 4.2 (t, 1H, J=9 Hz, —S—CH—C=O), 7.0–8.0 (broad m, 4H).

Elementary analysis:

|  | C (%) | H (%) | N (%) |
| --- | --- | --- | --- |
| Calculated: | 58.07 | 4.06 | 5.64 |
| Found: | 58.16 | 4.22 | 5.81 |

EXAMPLE 2

A 20 g quantity of N-oxydiethylene-2-benzothiazolylsulfenamide is dissolved in 60 ml of benzene, and the solution is heated to about 50° C. Subsequently 3 ml of acetic acid is added to the solution, and 12.7 g of cyclopentanone is further added thereto at a time. The mixture is allowed to react at the same temperature for 12 hours with stirring. The reaction mixture is cooled to room temperature, washed with water and thereafter distilled in vacuo to remove the solvent. The residue is extracted with 10% aqueous solution of hydrochloric acid three times. The condensation product dissolved in the aqueous solution of hydrochloric acid is neutralized with sodium bicarbonate and then reextracted with ethyl acetate. The extract is dried over magnesium sulfate and filtered. Concentration of the filtrate in vacuo gives 17 g of 2-(benzothiazolyl-2-mercapto)cyclopentanone in the form of white crystals, yield 90%.

Melting point: 115°–116° C.

The IR and NMR absorption spectra coincide well with the results achieved in Example 1. Elementary analysis:

|  | C (%) | H (%) | N (%) |
| --- | --- | --- | --- |
| Calculated: | 58.07 | 4.06 | 5.64 |
| Found: | 58.21 | 4.09 | 5.71 |

EXAMPLE 3

A 20 g quantity of N-ethyl-2-benzothiazolylsulfenamide is dissolved in 50 ml of tetrahydrofuran, and the solution is heated to about 50° C. Subsequently 1 g of acetic acid is added to the solution, and 13.5 g of cyclopentanone is further added thereto at a time. The same procedure as in Example 1 is thereafter repeated to obtain 16 g of 2-(benzothiazolyl-2-mercapto)cyclopentanone in the form of white crystals, yield 70%. Melting point: 115°–116° C.

The IR and NMR absorption spectra coincide well with the results achieved in Example 1. Elementary analysis:

|  | C (%) | H (%) | N (%) |
|---|---|---|---|
| Calculated: | 58.07 | 4.06 | 5.64 |
| Found: | 58.21 | 4.03 | 5.72 |

EXAMPLE 4

A 3.0 ml quantity of allyl bromide is added to a mixture of 5.5 g of 2-(benzothiazolyl-2-mercapto)-cyclopentanone, 8 g of potassium carbonate and 100 ml of acetone with full stirring, and the resulting mixture is refluxed with heating for 12 hours. On completion of the reaction, the acetone is distilled off. The residue is extracted with ethyl acetate, and the extract is washed with water, then dried over magnesium sulfate and thereafter filtered. The filtrate is concentrated to give a residue, which is then distilled at reduced pressure of 0.002 mmHg, affording 6 g of 2-allyl-2-(benzothiazolyl-2-mercapto)cyclopentanone (yield: 94%).

Boiling point: 81°–83° C. (0.002 mmHg).

IR (neat): 3060, 2970, 2925, 2850, 1735, 1640, 1455, 1425, 1410, 1310, 1270, 1235, 1155, 1140, 1125, 1075, 1015, 990, 920, 755, 720, 675 cm.$^{-1}$ NMR (CCl$_4$): $\delta$1.6–3.0 (broad m, 6H, —CH$_2$—), 4.7–6.2 (broad m, 3H, —CH=CH$_2$), 7.0–8.0 (broad m, 4H)

Elementary analysis:

|  | C (%) | H (%) | N (%) |
|---|---|---|---|
| Calculated: | 70.02 | 5.88 | 5.44 |
| Found: | 70.10 | 5.81 | 5.35 |

EXAMPLE 5

A 1.5 ml quantity of 2-pentynyl bromide is added to a mixture of 3.3 g of 2-(benzothiazolyl-2-mercapto)cyclopentanone, 7.5 g of potassium carbonate, 0.5 g of potassium iodide and 100 ml of acetone with full stirring, and the resulting mixture is refluxed with heating for 12 hours. On completion of the reaction, the same procedure as in Example 4 is repeated, giving 4.2 g of 2-pentynyl-2-(benzothiazolyl-2-mercapto)cyclopentanone (yield: 90%).

Boiling point: 88°–89° C. (0.001 mmHg).

IR (neat): 1970, 1745, 1435, 1315, 990, 760, 730 cm.$^{-1}$

NMR (CCl$_4$): $\delta$1.11 (t, J=7 Hz, 3H, CH$_3$), 1.60–2.80 (broad m, 8H, —CH$_2$—), 2.88 (m, 2H, —C≡C—CH$_2$—), 6.9–8.2 (broad m, 4H)

Elementary analysis:

|  | C (%) | H (%) | N (%) |
|---|---|---|---|
| Calculated: | 72.07 | 6.05 | 4.94 |
| Found: | 72.15 | 6.00 | 4.87 |

EXAMPLE 6

Propargyl bromide (10 ml) and 0.5 g of lithium iodide are added to a mixture of 1.83 g of 2-(benzothiazolyl-2-mercapto)cyclopentanone, 4.7 g of potassium carbonate and 30 ml of acetone with full stirring, and the resulting mixture is refluxed with heating for 12 hours. On completion of the reaction, the same procedure as in Example 4 is repeated, affording 2.0 g of 2-propargyl-2-(benzothiazolyl-2-mercapto)cyclopentanone (yield: 95%).

Boiling point: 77°–79° C. (0.001 mmHg).

IR (neat): 3285, 2950, 2120, 1740, 1425, 1315, 1155, 985, 760 cm.$^{-1}$

NMR (CCl$_4$): $\delta$1.91 (m, 1H), 1.7–3.0 (broad m, 6H), 3.0 (m, 2H), 7.0–8.0 (broad m, 4H).

Elementary analysis:

|  | C (%) | H (%) | N (%) |
|---|---|---|---|
| Calculated: | 70.58 | 5.13 | 5.49 |
| Found: | 70.50 | 5.12 | 5.48 |

EXAMPLE 7

A 1.6 g quantity of cis-2-pentenyl iodide is added to a mixture of 2.4 g of 2-(benzothiazolyl-2-mercapto)-cyclopentanone, 4.0 g of potassium carbonate and 50 ml of methyl ethyl ketone with full stirring, and the resulting mixture is refluxed with heating for 10 hours. On completion of the reaction, the same procedure as in Example 4 is repeated to give 2.75 g of 2-(cis-2-pentenyl)-2-(benzothiazolyl-2-mercapto)cyclopentanone (yield: 90%).

Boiling point: 89°–90° C. (0.0015 mmHg).

IR (neat): 2970, 1740, 760 cm.$^{-1}$

NMR (CDCl$_3$): $\delta$1.1 (t, 3H), 6.9–8.2 (broad m, 4H), 5.4 (m, 2H).

Elementary analysis:

|  | C (%) | H (%) | N (%) |
|---|---|---|---|
| Calculated: | 71.56 | 6.71 | 4.91 |
| Found: | 71.41 | 6.70 | 4.88 |

EXAMPLE 8

A 2.3 g quantity of pentyl bromide is added to a mixture of 3.0 g of 2-(benzothiazolyl-2-mercapto)-cyclopentanone, 7.5 g of potassium carbonate, 0.5 g of potassium iodide and 80 ml of acetone with full stirring, and the resulting mixture is refluxed with heating for 20 hours. On completion of the reaction, the same procedure as in Example 4 is repeated, giving 2.7 g of 2-pentyl-2-(benzothiazolyl-2-mercapto)cyclopentanone (yield: 75%).

Boiling point: 84°–85° C. (0.001 mmHg).

IR (neat): 1740, 760 cm.$^{-1}$

NMR (CDCl$_3$): $\delta$1.1 (t, 3H), 6.9–8.2 (broad m, 4H).

Elementary analysis:

|  | C (%) | H (%) | N (%) |
|---|---|---|---|
| Calculated: | 71.06 | 7.37 | 4.87 |
| Found: | 71.12 | 7.35 | 4.95 |

REFERENCE EXAMPLE 1

A 4.5 g quantity of 2-allyl-2-(benzothiazolyl-2-mercapto)cyclopentanone is dissolved in 10 ml of tetrahydrofuran, and 0.3 g of p-toluenesulfonic acid is added to the solution. The mixture is fully stirred. The solvent is distilled off, and the residue is heated to 110° C. in a nitrogen stream, affording 1.6 g of 2-allyl-2-cyclopentenone in the form of a colorless oil (yield: 75%).

Boiling point: 50°–53° C. (0.05 mmHg).

IR (neat): 1700, 1640, 1645 cm.$^{-1}$

NMR (CDCl$_3$): $\delta$1.75–3.00 (m, 6H), 4.75–6.10 (m, 3H), 7.50 (m, 1H).

Elementary analysis:

| | C (%) | H (%) |
|---|---|---|
| Calculated: | 78.65 | 8.25 |
| Found: | 78.61 | 8.26 |

REFERENCE EXAMPLE 2

A 3.0 g quantity of 2-propargyl-2-(benzothiazolyl-2-mercapto)cyclopentanone is dissolved in 10 ml of tetrahydrofuran, and 0.1 g of p-toluenesulfonic acid is added to the solution. The mixture is thoroughly stirred. The solvent is distilled off, and the residue is heated to 120° C. in a vacuum (17 mmHg), giving 1.2 g of 2-propargyl-2-cyclopentenone as a colorless oily fraction (yield: 82%).

Boiling point 53°–55° C. (0.02 mmHg).
IR (neat): 3280, 1705, 1645, 795 cm.$^{-1}$
NMR (CCl$_4$): δ1.97 (m, 1H), 3.0 (m, 2H), 7.50 (broad m, 1H).

Elementary analysis:

| | C (%) | H (%) |
|---|---|---|
| Calculated: | 79.97 | 6.71 |
| Found: | 79.91 | 6.68 |

REFERENCE EXAMPLE 3

A 5.5 g quantity of 2-(2-pentynyl)-2-(benzothiazolyl-2-mercapto)cyclopentanone is dissolved in 10 ml of tetrahydrofuran, and 0.2 g of p-toluene-sulfonic acid is added to the solution. The mixture is thoroughly stirred. The solvent is distilled off, and the residue is heated to 120° C. in a vacuum (17 mmHg), affording 2.4 g of 2-(2-pentynyl)-2-cyclopentenone as a colorless oily fraction (yield: 88%).

Boiling point: 65°–68° C. (0.01 mmHg).
IR (neat): 1705, 1625 cm.$^{-1}$
NMR (CDCl$_4$): δ1.12 (t, J=7 Hz, 3H), 1.75–3.00 (m, 6H), 2.94 (m, 2H), 7.40 (m, 1H).

Elementary analysis:

| | C (%) | H (%) |
|---|---|---|
| Calculated: | 81.04 | 8.16 |
| Found: | 81.12 | 8.10 |

REFERENCE EXAMPLE 4

A 2.75 g quantity of 2-(cis-2-pentenyl)-2-(benzothiazolyl-2-mercapto)cyclopentanone is dissolved in 30 ml of toluene, and 0.1 g of p-toluenesulfonic acid is added to the solution. The mixture is thoroughly stirred and refluxed with heating for 30 minutes. On completion of the reaction, the mixture is cooled to room temperature and washed with an aqueous solution of sodium bicarbonate. The solvent is distilled off. The residue is distilled in a vacuum, giving 1.15 g of 2-(cis-2-pentenyl)-2-cyclopentenone as a fraction at 67° to 69° C. (0.02 mmHg), yield 85%.

Boiling point: 67°–69° C. (0.02 mmHg).
IR (neat): 1700, 1630, 1350, 970 cm.$^{-1}$ NMR (CDCl$_3$): δ1.00 (t, 3H), 1.75–3.00 (m, 8H), 5.40 (m, 2H), 7.15 (m, 1H).

Elementary analysis:

| | C (%) | H (%) |
|---|---|---|
| Calculated: | 79.96 | 9.39 |
| Found: | 79.89 | 9.32 |

REFERENCE EXAMPLE 5

A 1.0 g quantity of 2-pentyl-2-(benzothiazolyl-2-mercapto)cyclopentanone is dissolved in 10 ml of dimethylformamide. The solution is heated at 120° C. for 20 hours for thermal decomposition. On completion of the reaction, the resulting mixture is extracted with ether, and the extract is washed with water, dried over magnesium sulfate and filtered. Concentration of the filtrate gives a residue, which is then distilled in a vacuum (0.04 mmHg), affording 0.34 g of 2-pentyl-2-cyclopentenone as a fraction at 64° to 66° C. (yield: 70%).

Boiling point: 64°–66° C. (0.04 mmHg).
IR (neat): 1700, 1000, 920 cm.$^{-1}$
NMR (CCl$_4$): δ0.67–1.60 (m, 9H), 1.70–2.65 (m, 6H), 7.17 (m, 1H).

Elementary analysis:

| | C (%) | H (%) |
|---|---|---|
| Calculated: | 78.90 | 10.59 |
| Found: | 78.81 | 10.51 |

What is claimed is:

1. A 2-substituted-cyclopentanone compound represented by the formula

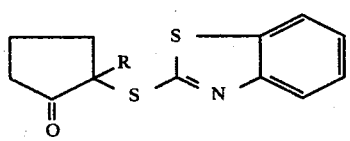

(I)

wherein R is hydrogen, alkyl having from 3 to 6 carbon atoms, alkenyl having from 3 to 6 carbon atoms or alkynyl having from 3 to 6 carbon atoms.

2. The compound as defined in claim 1 wherein R is hydrogen.

3. The compound of claim 1, 2-pentynyl-2-(benzothiazolyl-2-mercapto)cyclopentanone.

4. A 2-substituted-cyclopentanone compound represented by the formula

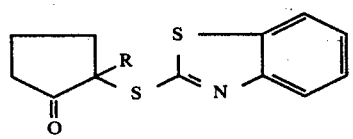

(I)

wherein R is alkyl having from 3 to 6 carbon atoms, alkenyl having from 3 to 6 carbon atoms or alkynyl having from 3 to 6 carbon atoms.

* * * * *